US005716374A

United States Patent [19]

Francese et al.

[11] Patent Number: 5,716,374
[45] Date of Patent: Feb. 10, 1998

[54] STAMPED CLEVIS FOR ENDOSCOPIC INSTRUMENTS AND METHOD OF MAKING THE SAME

[75] Inventors: Jose L. Francese; Juergen Andrew Kortenbach, both of Miami Springs, Fla.

[73] Assignee: Symbiosis Corporation, Miami, Fla.

[21] Appl. No.: 541,617

[22] Filed: Oct. 10, 1995

[51] Int. Cl.$^6$ .................................................. A61B 17/28
[52] U.S. Cl. ........................... 606/207; 606/205; 128/751
[58] Field of Search ................................. 128/751, 752; 606/205, 206, 207, 170, 174; 72/379.2; 29/897, 434, 525.11, 525.02

[56] References Cited

U.S. PATENT DOCUMENTS

| | | | |
|---|---|---|---|
| 1,502,133 | 7/1924 | Anderson | 29/897 |
| 2,793,028 | 5/1957 | Wheeler | 29/897 |
| 4,971,067 | 11/1990 | Bolduc et al. | 128/751 |
| 5,172,700 | 12/1992 | Bencini et al. | 128/751 |
| 5,238,002 | 8/1993 | Devlin et al. | 606/205 |
| 5,267,998 | 12/1993 | Hagen | 606/45 |

Primary Examiner—Michael Buiz
Assistant Examiner—Patrick W. Rasche
Attorney, Agent, or Firm—David P. Gordon

[57] ABSTRACT

A stamped clevis is made from a stainless steel sheet which is cut (stamped) to form at least one relatively narrow distally extending arm and at least one relatively broad proximal base. The distal arm is provided with at least one mounting hole for receiving an axle pin and the proximal portion is wrapped to form a cylinder or a broken cylinder. In one embodiment, the sheet is cut to form two relatively broad proximal bases and two relatively narrow substantially parallel distal arms, one arm extending from each base and being provided with a mounting hole. The arms are joined by a cross member proximal of the mounting holes and a central tab having a third mounting hole extends distally from the cross member. The cut sheet is formed by bending the cross member on either side of the tab in an "S" configuration so that the mounting holes are aligned substantially coaxially. The two proximal bases are bent towards each other to form a bifurcated cylinder. The tab may be provided with an integral spike. In another embodiment, the sheet is cut to form a central tab with a mounting hole and a distally extending spike and a pair of relatively broad proximal bases. The bases are bent in opposite directions to form a substantially cylindrical member having an "S-shaped" section adjacent to the central tab. In another embodiment two arms extend from a single base.

30 Claims, 4 Drawing Sheets

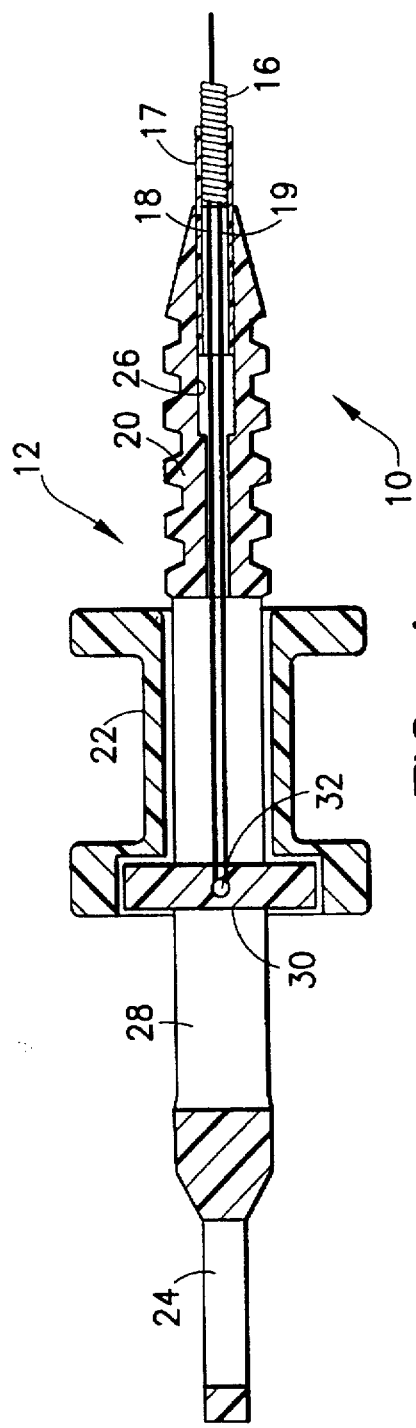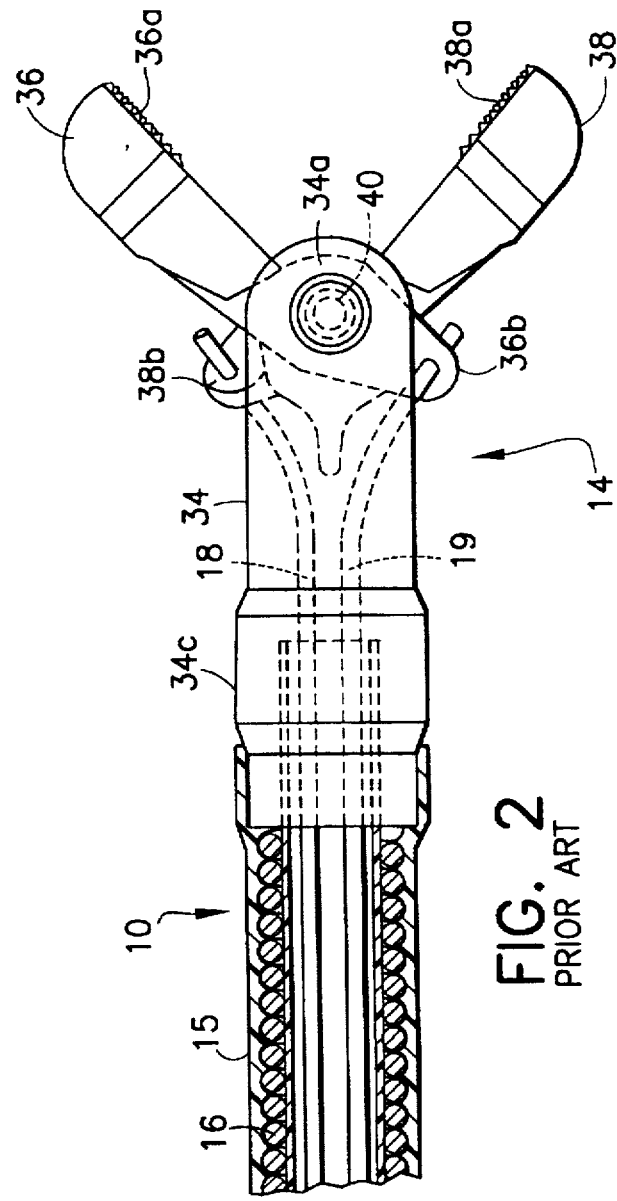
FIG. 1
PRIOR ART
FIG. 2
PRIOR ART

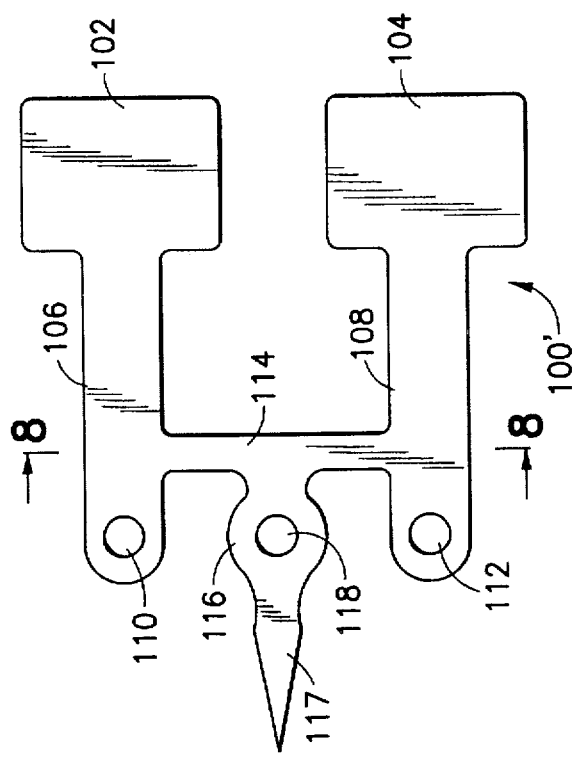
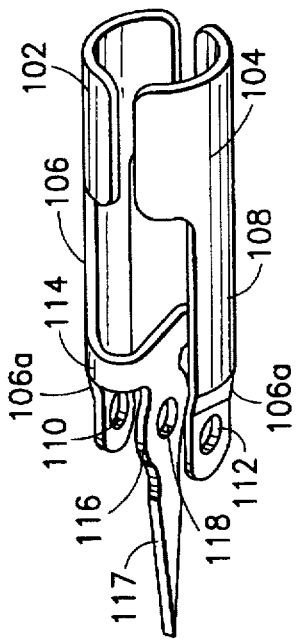
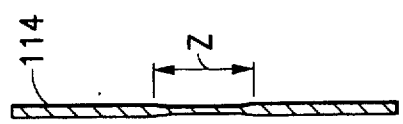
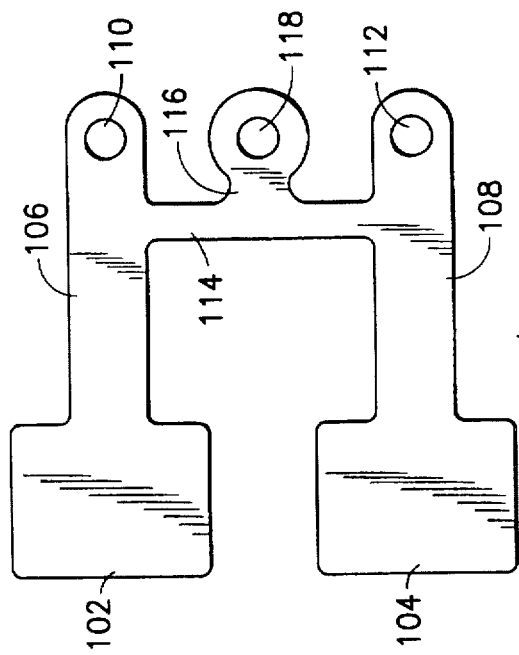
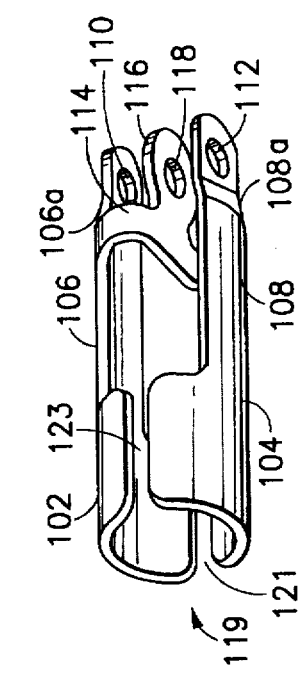

STAMPED CLEVIS FOR ENDOSCOPIC INSTRUMENTS AND METHOD OF MAKING THE SAME

BACKGROUND OF THE INVENTION

1. Field of the invention

The invention relates to endoscopic instruments. More particularly, the invention relates to clevises which are stamped from a sheet material and progressively formed to obtain a substantially cylindrical end and at least one clevis arm. The invention is particularly useful in conjunction with endoscopic biopsy forceps although it is not limited thereto. For purposes herein, the term "endoscopic" is to be understood in its broad sense to include laparoscopic, arthroscopic, and other microsurgical instruments whether or not used with an endoscope. In addition, as used herein the term "clevis" means a member for rotatably coupling at least one end effector to the distal end of an endoscopic instrument, and not necessarily a U-shaped member.

2. State of the Art

Endoscopic biopsy forceps are medical instruments which are used in conjunction with an endoscope for taking tissue samples from the human body for analysis. As seen in FIGS. 1–4, a prior art endoscopic biopsy forceps instrument 10 generally includes a proximal handle 12, a distal end effector assembly 14, and a long, slender, flexible coil 16. The coil, which is typically 8 feet long and several millimeters in diameter, has a pair of axially displaceable control wires 18, 19 extending therethrough and coupled to the handle 12 and the end effector assembly 14. The coil 16 is preferably covered with a PTFE, FEP or polyolefin sheath 15 along substantially all of its length, and a strain relief sleeve 17 may be provided to cover a proximal portion of the coil which extends from the handle 12. The control wires 18, 19 are preferably flexible but longitudinally inelastic and are ideally formed from 304 steel.

The proximal handle 12 includes a central shaft 20 and a displaceable spool 22. The proximal end of the shaft 20 is provided with a thumb ring 24 and a longitudinal bore 26 is provided at the distal end of the shaft 20. A longitudinal slot 28 extends from the proximal end of bore 26 to a point distal of the thumb ring 24. The displaceable spool 22 is provided with a cross member 30 which passes through the slot 28 in the central shaft 20. The cross member 30 is provided with a coupling means 32 for attaching the proximal ends of the control wires 18, 19.

The end effector assembly 14 includes a clevis 34 which is coupled to the distal end of the coil 16, and a pair of forceps jaws 36, 38. The clevis 34 has a pair of clevis arms 34a, 34b between which the jaws 36, 38 are rotatably mounted on an axle pin 40. Each jaw 36, 38 is provided with a distal cutting edge 36a, 38a, a proximal tang 36b, 38b, and a mounting hole 36c, 38c therebetween. The proximal tangs 36b, 38b are each coupled to the distal end of a respective control wire 18, 19. From the foregoing, those skilled in the art will appreciate that relative movement of the shaft 20 and spool 22 results in movement of the control wires 18, 19 relative to the coil 16. Such action results in opening and closing of the jaws 36, 38. Optionally, as shown in FIG. 3, an end effector assembly 14" may also include a flat knife or spike which is mounted between the jaws 36, 38.

As seen best in FIG. 4, the tang of each jaw is offset from the centerline CL of the jaw cup, thereby permitting the jaw 36 to be substantially identical to jaw 38. The clevis 34 is typically formed as a unitary molded or cast member and has a substantially cylindrical proximal end 34c from which the clevis arms 34a, 34b extend. The proximal end 34c of the clevis 34 is crimped or welded to the distal end of the coil 16.

The endoscopic biopsy procedure is accomplished through an endoscope which is inserted into a body and guided by manipulation to the biopsy site. The endoscope typically includes a long narrow flexible tube with an optical lens and a narrow lumen for receiving a biopsy forceps. The practitioner guides the endoscope to the biopsy site while looking through the optical lens and inserts the biopsy forceps through the lumen of the endoscope to the biopsy site. While viewing the biopsy site through the optical lens of the endoscope, the practitioner manipulates the actuating handle to effect a tissue sampling operation at the distal end of the instrument. After a sample has been obtained, the practitioner and/or an assistant carefully withdraws the instrument from the endoscope while holding the actuating handle to maintain the jaws in a closed position.

It is understood that in order to be effective in obtaining a biopsy sample, the cutting edge of the forceps jaws should be very sharp. Moreover, the entire end effector assembly should be relatively durable since it may be necessary to apply considerable force to the end effector assembly in order to obtain a biopsy sample. However, due to the small size of the end effector assembly (typically a few millimeters in diameter), durable components are expensive to manufacture. The presently preferred method of making a clevis and end effectors is by investment casting of bronze or other suitable material, although other methods such as molding and machining are also known in the art.

SUMMARY OF THE INVENTION

It is therefore an object of the invention to provide a durable clevis for use in an endoscopic biopsy forceps instrument.

It is also an object of the invention to provide a durable clevis which is inexpensive to manufacture.

It is another object of the invention to provide a method of making an inexpensive yet durable clevis for use in an endoscopic biopsy forceps instrument.

In accord with these objects which will be discussed in detail below, the stamped clevis of the present invention is preferably made from a stainless steel sheet which is cut (stamped) to form at least one relatively narrow distally extending arm and at least one relatively broad proximal base. The distal arm is provided with at least one mounting hole for receiving an axle pin and the proximal portion is wrapped to form a cylinder or a broken cylinder. According to a presently preferred first embodiment of the invention, a stainless steel sheet is cut to form two relatively broad proximal bases and two relatively narrow substantially parallel distal arms, one arm extending from each base. The distal end of each arm is provided with a mounting hole and the arms are joined by a substantially orthogonal cross member proximal of the mounting holes. Preferably, a central tab extends distally from the cross member and is provided with a third mounting hole. The cut sheet is formed by bending the cross member on either side of the central tab in an "S" configuration so that the mounting holes are aligned substantially coaxially. The two proximal bases are bent towards each other to form a bifurcated cylinder. The bifurcated cylinder can be crimped or welded to the distal end of a coil and tangs of jaws can be mounted between the central tab and a respective arm on an axle pin which passes through the three holes. In an alternative first embodiment of the invention, the steel sheet is cut so that a distal spike extends from the central tab.

According to a second embodiment of the invention, a stainless steel sheet is cut to form a single central tab with a distally extending spike and a pair of relatively broad proximal bases. The bases are bent in opposite directions to form a substantially cylindrical member having an "S-shaped" section adjacent to the central tab. The central tab is provided with a single mounting hole for receiving an axle pin so that jaws may be mounted on either side of the tab with the spike extending between the jaws. The proximal cylindrical portion may be crimped or welded to the distal end of a coil.

According to a third embodiment of the invention, a stainless steel sheet is cut to form two substantially parallel distal arms extending from a single base. Each arm is provided with a distal mounting hole. The base is wrapped to form a cylinder or a broken cylinder with the arms parallel and the mounting holes substantially coaxial. A pair of jaws can be mounted between the distal arms and the proximal cylinder can be crimped or welded to the distal end of a coil.

Additional objects and advantages of the invention will become apparent to those skilled in the art upon reference to the detailed description taken in conjunction with the provided figures.

BRIEF DESCRIPTION OF THE DRAWINGS

FIG. 1 is an enlarged broken side elevation view in partial section of the proximal end of a prior art biopsy forceps instrument;

FIG. 2 is an enlarged broken side elevation view in partial section of the distal end of a prior art biopsy forceps instrument;

FIG. 5 is an enlarged plan view of a first embodiment of a stamped clevis according to the invention prior to forming;

FIG. 6 is an enlarged perspective view of the clevis of FIG. 5 after forming;

FIG. 7 is an enlarged plan view of an alternate first embodiment of a stamped clevis according tot he invention prior to forming;

FIG. 8 is a sectional view taken along line 8—8 of FIG. 7;

FIG. 9 is an enlarged perspective view of the clevis of FIG. 7 after forming;

DETAILED DESCRIPTION OF THE PREFERRED EMBODIMENTS

Figure 3:
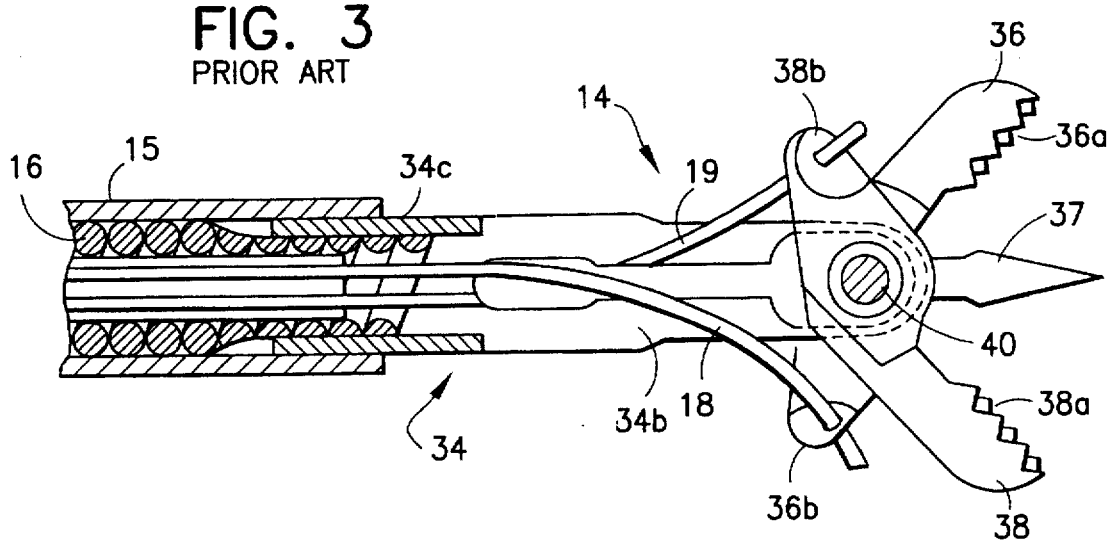
FIG. 3 is a view similar to FIG. 2 of the distal end of a prior art biopsy forceps instrument incorporating a spike between the forceps jaws.
Figure 4:
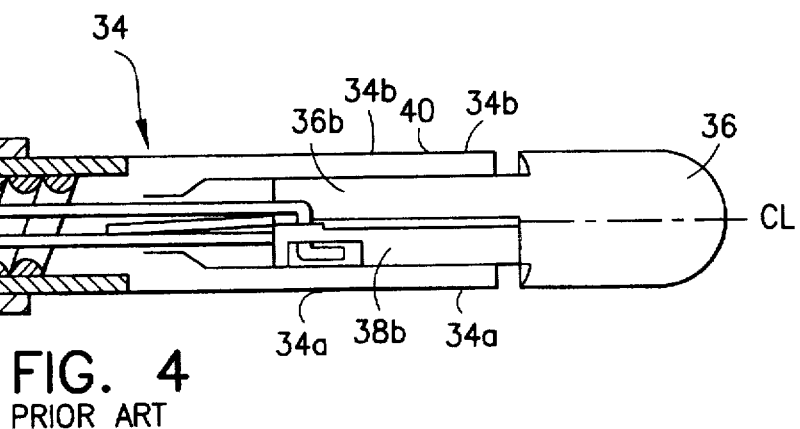
FIG. 4 is an enlarged top plan view in partial section of the distal end of a prior art biopsy forceps instrument.
Figure 6A:
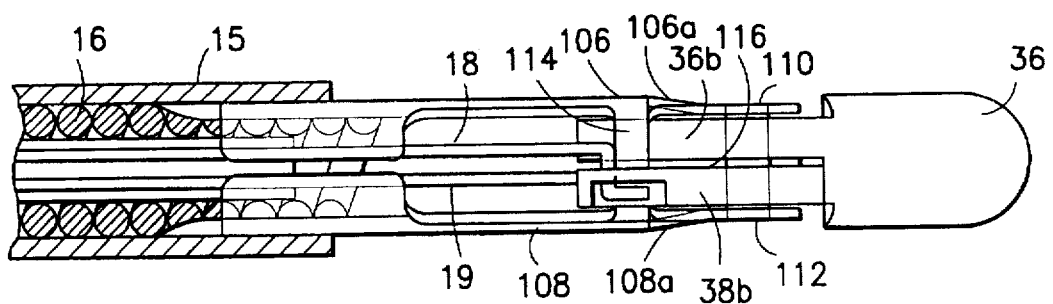
FIG. 6a is an enlarged partially transparent top view in partial section of the clevis from FIGS. 5 and 6 as part of the distal end of a biopsy forceps instrument.

Referring now to FIGS. 5, 6, and 6a, a first embodiment a stamped clevis 100 according to the invention is made from a stainless steel sheet preferably approximately 0.007 inches thick and cut to the pattern shown in FIG. 5. More particularly, the sheet is cut to form two relatively broad proximal bases 102, 104 and two relatively narrow substantially parallel distal arms 106, 108, one arm extending from each base. The distal end of each arm is provided with a mounting hole 110, 112 and the arms are joined by a substantially orthogonal cross member 114 proximal of the mounting holes. The cross member 114 is preferably provided with a central tab 116 which extends distally from the cross member and is provided with a third mounting hole 118. The stamped clevis 100 is then formed by bending the cross member 114 on either side of the central tab 116 in an "S" configuration so that the mounting holes 110, 112, and 118 are aligned substantially coaxially. The two proximal bases 102, 104 are bent towards each other to form a bifurcated cylinder having a proximal opening 119 and slits 121, 123. The bifurcated cylinder can be crimped or welded to the distal end of a coil 16 as shown in FIG. 6a, and the tangs 36b, 38b of jaws 36, 38 can be mounted between the central tab 116 and a respective arm 106, 108. As shown in FIG. 6, the formed clevis 100 has an overall length of approximately 0.3 inches and the bifurcated cylinder formed by the bases 102, 104 has an overall diameter of approximately 0.09 inches. According to a preferred aspect of this embodiment, the arms 106, 108 are bent inward at an angle of approximately 15° along a portion 106a, 108a just proximal of the mounting holes 110, 112. An alternate first embodiment of a stamped clevis 100' is shown in FIGS. 7 through 9. This embodiment of the invention is substantially identical to the first embodiment with identical reference numerals referring to identical features. The difference between this embodiment and the first embodiment is a spike 117 which is formed on the central tab 116 and extends distally therefrom for a distance of approximately 0.135 inches from the center of the hole 118. In order to provide the spike 117 with a relatively sharp knife-like quality, a zone "Z" in the center of the cross member 114 is coined on both sides with a smooth taper to a thickness of approximately 0.005 inches. The clevis 100' is formed in the same manner as the clevis 100 to the shape shown in FIG. 9.

Figure 10:
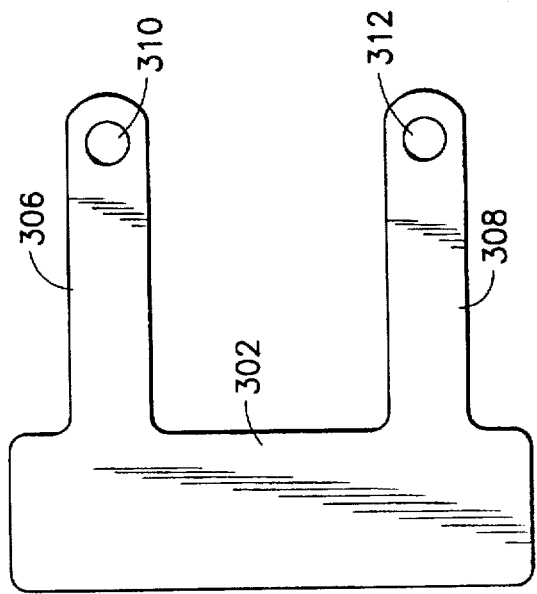
FIG. 10 is an enlarged plan view of a second embodiment of a stamped clevis according to the invention prior to forming.
Figure 11:
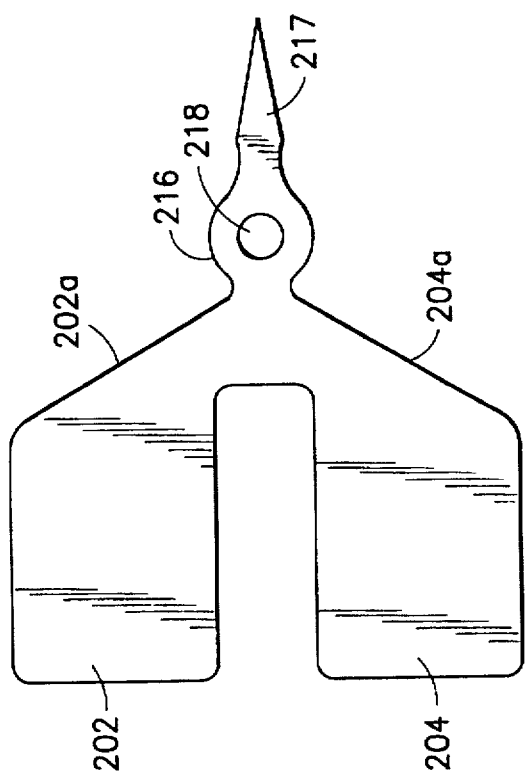
FIG. 11 is an enlarged top plan view of the clevis of FIG. 10 after forming.

According to a second embodiment of the invention, shown in FIGS. 10 and 11, a clevis 200 is formed from a stainless steel sheet which is cut to form a pair of relatively broad proximal bases 202, 204 with a single central tab 216 having a distally extending spike 217 and a mounting hole 218. The bases 202, 204 are preferably provided with angled distal edges 202a, 204a which ramp proximally away from the central tab 216. The clevis 200 is formed by bending the bases 202, 204 in opposite directions to form a substantially cylindrical member having an "S-shaped" section adjacent to the central tab 216. When formed into a cylindrical member, the angled distal edges 202a, 204a form distal spiral sections which provide room for the movement of tangs of jaws coupled to the central tab 216. Those skilled in the art will appreciate that in order to assure sufficient strength, in this embodiment of the clevis, the mounting hole must be located relatively close to the cylindrical portion. Therefore, in order to provide room for jaw tangs, portions of the cylindrical portion must be cut back as shown. The proximal cylindrical portion may be crimped or welded to the distal end of a coil.

Figure 12:
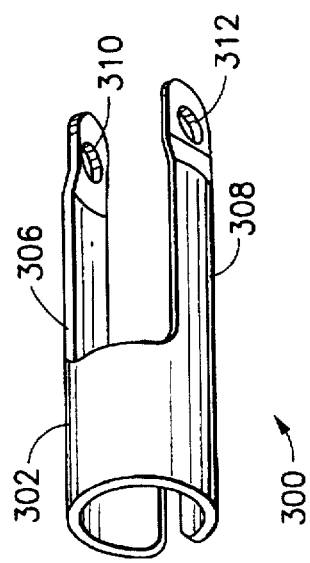
FIG. 12 is an enlarged plan view of a third embodiment of a stamped clevis according to the invention prior to forming.
Figure 13:
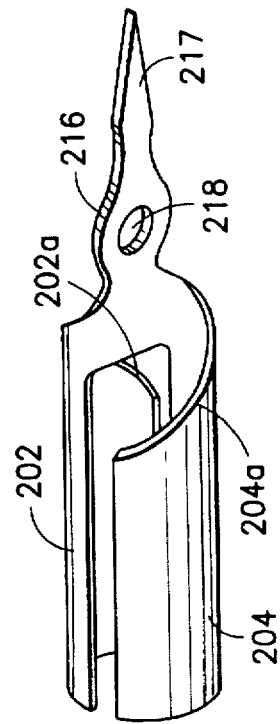
FIG. 13 is an enlarged perspective view of the clevis of FIG. 12 after forming.

According to a third embodiment of the invention, shown in FIGS. 12 and 13, a clevis 300 is formed from a stainless steel sheet which is cut to form a single base 302 with two substantially parallel distal arms 306, 308 extending therefrom. Each arm is provided with a distal mounting hole 310, 312. The base 302 is wrapped to form a cylinder or a broken cylinder with the arms 306, 306 parallel and the mounting holes 310, 312 substantially coaxial. A pair of jaws can be mounted between the distal arms and the proximal cylinder can be crimped or welded to the distal end of a coil.

There have been described and illustrated herein several embodiments of a stamped clevis for an endoscopic instrument and methods of making the same. While particular embodiments of the invention have been described, it is not intended that the invention be limited thereto, as it is intended that the invention be as broad in scope as the art will allow and that the specification be read likewise. Thus, while particular dimensions and materials have been disclosed, it will be appreciated that other dimensions and materials could be utilized. Also, while cylindrical portions have been shown as incomplete or broken cylinders, it will be recognized that welding, soldering, brazing, or other operations may be used to complete the cylindrical portions if desired. Further, while the clevis was shown with respect to use in a biopsy forceps instrument, it will be appreciated that the clevis could be used as part of an endoscopic clamp, scissors, dissectors, etc., and that the proximal cylindrical end of the clevis can be coupled to a hollow tube or a flexible coil. Moreover, while particular configurations have been disclosed in reference to the mounting holes and the spike, it will be appreciated that other configurations could be used as well. It will therefore be appreciated by those skilled in the art that yet other modifications could be made to the provided invention without deviating from its spirit and scope as so claimed.

We claim:

1. A clevis for use in an endoscopic instrument having a coil or tube, said clevis comprising at least one distally extending arm having a distal mounting hole and at least one proximal base, said clevis being formed by the process of cutting sheet material into a form with said at least one arm and said at least one base and rolling said at least one base to form a substantially cylindrical proximal portion of said clevis which couples to the coil or tube, wherein
   said at least one arm consists of one arm,
   said at least one base includes two bases extending on opposite sides of said one arm, and
   said two bases are wrapped to form said substantially cylindrical portion.

2. A clevis according to claim 1, wherein:
   each of said two bases have an angled distal edge which ramps proximally away from said one arm.

3. A clevis according to claim 1, wherein:
   said one arm has an integral distally extending spike.

4. A clevis according to claim 3, wherein:
   said sheet material is approximately 0.007 inches thick and is coined on both sides in the vicinity of said tab and said spike to approximately 0.005 inches thick.

5. A clevis according to claim 1, wherein:
   said two bases form an S configuration adjacent to said one arm.

6. A clevis according to claim 1, wherein:
   said sheet material is stainless steel.

7. A clevis according to claim 6, wherein:
   said sheet material is approximately 0.007 inches thick.

8. A clevis for use in an endoscopic instrument, said clevis comprising:
   a) two substantially parallel arms, each having a distal mounting hole;
   b) a substantially cylindrical base with said two arms extending distally from said base; and
   c) a cross member coupling said two substantially parallel arms, said cross member being bent into an S configuration.

9. A clevis according to claim 8, wherein:
   said substantially cylindrical base is comprised of two portions, each of said two portions being wrapped toward each other.

10. A clevis according to claim 9, wherein:
    said cross member includes a central tab having a third mounting hole and said cross member is bent on either side of said tab into said S configuration so that all of said mounting holes are aligned substantially coaxially.

11. A clevis according to claim 10, wherein:
    said central tab has an integral distally extending spike.

12. A clevis for use in an endoscopic instrument, said clevis comprising:
    a) a substantially cylindrical proximal base having a distal cross member which crosses through a substantially cylindrical space which is a longitudinal projection of said base; and
    b) an arm extending distally from said distal cross member.

13. A clevis according to claim 12, wherein:
    said base comprises a pair of proximal base portions joined to each other at their distal ends by said distal cross member.

14. A clevis according to claim 13, wherein:
    each of said proximal base portions has an angled distal edge.

15. A clevis according to claim 12, wherein:
    said arm defines a mounting hole.

16. A clevis according to claim 12, wherein:
    said arm is spike shaped.

17. A clevis according to claim 12, wherein:
    a cross section through said cross member and a distal portion of said base exhibits a substantially S configuration.

18. A method of making a clevis for an endoscopic biopsy forceps instrument having a coil or tube with a distal end, said method comprising:
    a) cutting a sheet material to form at least one proximal base, at least one arm extending distally from the base, and a distal cross member, said at least one arm being relatively narrow as compared to said at least one base;
    b) forming a distal mounting hole in the at least one arm; and
    c) rolling the at least one base to form a substantially cylindrical portion of the clevis such that the distal cross member crosses through a substantially cylindrical space which is a longitudinal projection of the cylindrical portion of the clevis.

19. A method according to claim 18, further comprising:
    d) cutting the sheet material to form two bases, each base having an arm extending distally therefrom, and a cross member extending between said arms;
    e) bending the cross member in an S configuration; and
    f) rolling both of the bases to form the substantially cylindrical portion.

20. A method according to claim 19, further comprising:
    g) forming a distal mounting hole in each of the arms; and
    h) bending the cross member so that the holes are aligned substantially coaxially.

21. A method according to claim 20, further comprising:
    i) cutting the sheet material to form a central tab extending distally from the cross member;

j) forming a third mounting hole in the tab; and k) bending the cross member so that all of the holes are aligned substantially coaxially.

22. A method according to claim 21, further comprising:

1) cutting the sheet material to form a spike extending distally from the central tab.

23. A method according to claim 18, further comprising:

d) cutting the sheet material to form two bases extending proximally from a single arm; and e) rolling both bases to form the substantially cylindrical portion.

24. A method according to claim 18, further comprising:

d) cutting the sheet material to form a single base with two distally extending arms; and e) rolling the single base to form the substantially cylindrical portion.

25. An endoscopic instrument, comprising:

a) a hollow tube having a proximal end and a distal end;

b) a control member extending through said hollow tube and having a proximal end and a distal end;

c) actuation means coupled to said proximal end of said hollow tube and said proximal end of said control member for effecting longitudinal displacement of said control member relative to said hollow tube;

d) a stamped and rolled clevis having a substantially cylindrical proximal end and at least one distally extending arm, said substantially cylindrical proximal end being coupled to said distal end of said hollow tube, said substantially cylindrical proximal end defining a substantially cylindrical longitudinal space extending infinitely along a longitudinal axis of said clevis, said clevis including a cross member which crosses through said longitudinal space; and e) at least one end effector rotatably coupled to said at least one arm and coupled to said distal end of said control member.

26. An endoscopic instrument according to claim 25, wherein:

said clevis has a substantially S-shaped section between said proximal end of said clevis and said at least one arm.

27. An endoscopic instrument according to claim 26, wherein:

said at least one arm includes an integral spike extending distally therefrom.

28. An endoscopic instrument according to claim 25, wherein:

said at least one arm comprises two arms, and said clevis further includes a substantially S-shaped cross member between said two arms.

29. An endoscopic instrument according to claim 28, wherein:

said cross member includes an integral spike extending distally therefrom.

30. An endoscopic instrument according to claim 28, wherein:

said cross member includes an integral distally extending tab, said tab and each of said two arms including mounting holes which are substantially coaxially aligned.

* * * * *